US012674157B2

(12) United States Patent
Lee et al.

(10) Patent No.: US 12,674,157 B2
(45) Date of Patent: Jul. 7, 2026

(54) TRANSPORT MEDIA FOR CLINICAL SPECIMEN COLLECTION AND MOLECULAR DIAGNOSTIC APPLICATIONS AND METHODS OF PRODUCTION AND USE THEREOF

(71) Applicant: Siemens Healthcare Diagnostics Inc., Tarrytown, NY (US)

(72) Inventors: Alex Hofai Lee, Fremont, CA (US); Qi Dang, Union City, CA (US); Jocelyn Lee, Castro Valley, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 781 days.

(21) Appl. No.: 17/907,202

(22) PCT Filed: Apr. 20, 2021

(86) PCT No.: PCT/US2021/070428
§ 371 (c)(1),
(2) Date: Sep. 23, 2022

(87) PCT Pub. No.: WO2021/217174
PCT Pub. Date: Oct. 28, 2021

(65) Prior Publication Data
US 2023/0121537 A1 Apr. 20, 2023

Related U.S. Application Data

(60) Provisional application No. 63/013,257, filed on Apr. 21, 2020.

(51) Int. Cl.
*C12N 15/10* (2006.01)
*C07C 51/02* (2006.01)
*C08K 5/31* (2006.01)
*C11D 3/04* (2006.01)

(52) U.S. Cl.
CPC .......... *C12N 15/1003* (2013.01); *C07C 51/02* (2013.01); *C08K 5/31* (2013.01); *C11D 3/042* (2013.01)

(58) Field of Classification Search
CPC ............ C12Q 1/6806; C12Q 2527/125; C12Q 2527/137; C12N 15/1003; C07C 51/02; C08K 5/31; A61B 10/0045; C11D 3/042
USPC ....................................................... 536/25.4
See application file for complete search history.

(56) References Cited

U.S. PATENT DOCUMENTS

| | | | |
|---|---|---|---|
| 9,212,399 | B2 | 12/2015 | Fischer et al. |
| 2005/0233333 | A1 | 10/2005 | Chomczynski |
| 2009/0312285 | A1 * | 12/2009 | Fischer ................ C12Q 1/6806 |
| | | | 435/5 |
| 2011/0054157 | A1 | 3/2011 | Bitner |
| 2011/0065108 | A1 | 3/2011 | Sherman et al. |
| 2011/0266172 | A1 | 11/2011 | Donner et al. |
| 2013/0122496 | A1 * | 5/2013 | Haydock .............. C12Q 1/6806 |
| | | | 435/6.12 |
| 2014/0193804 | A1 | 7/2014 | Fischer et al. |
| 2018/0258419 | A1 | 9/2018 | Fischer et al. |

FOREIGN PATENT DOCUMENTS

| | | |
|---|---|---|
| CN | 102575220 | 7/2012 |
| CN | 105682690 | 6/2016 |

OTHER PUBLICATIONS

International Search Report for PCT/US2021/070428 dated Jul. 16, 2021.
Cary-Blair Transport Medium, Dalynn Biologicals; Catalogue No. AN280; Oct. 2014.
ESwab Package Insert and How to use Guide, Copan, Feb. 2016.
MSwab Collection, Preservation and Transport System Product Insert and How to Use Guide, Copan, Dec. 2014.
Copan Universal Transport Medium (UTM-RT) System instructions for use; Copan; Jul. 2006.
ENAT Specimen Collection & Preservation, Copan, Apr. 2014.
510(k) Summary, Puritan Liquid Amies Collection and Transport System; Jun. 8, 2012.
Viral transport media (VTM) preparation; Standard Operating Procedures; Laboratorio de Genomica Viral y Humana; Facultad de Medicina UASLP; Creative Commons; May 17, 2017.

* cited by examiner

*Primary Examiner* — Ganapathy Krishnan

(57) ABSTRACT

A transport medium is disclosed that can be utilized for both sample collection and molecular diagnostic applications. The transport medium can be utilized with multiple types of biological samples and maintains the stability of nucleic acid present in the biological samples so that one or more nucleic acid assay target(s) present in the biological sample is not substantially degraded during storage and shipping. Also disclosed are kits containing the transport medium, mixtures that include a biological sample disposed in the transport medium, and methods of producing and using the medium.

13 Claims, No Drawings

TRANSPORT MEDIA FOR CLINICAL SPECIMEN COLLECTION AND MOLECULAR DIAGNOSTIC APPLICATIONS AND METHODS OF PRODUCTION AND USE THEREOF

CROSS-REFERENCE TO RELATED APPLICATIONS

This application is a 35 U.S.C. 371 national application of international application no. PCT/US2021/070428 filed 20 Apr. 2021, which claims priority of U.S. Provisional application No. 63/013,257 filed 21 Apr. 2020, the contents of which are fully incorporated herein by reference.

STATEMENT REGARDING FEDERALLY SPONSORED RESEARCH OR DEVELOPMENT

Not Applicable.

BACKGROUND

Biological samples that are collected in patients' homes, physicians' offices, clinics, hospitals, and/or even in a remote area may need to be preserved in a controlled environment, such as refrigeration, freezing, or chemical methods for one or more days or even one or more weeks before arrival at a central facility for high throughput analysis and/or screening. PCR analysis requires high quality of DNA/RNA, and minor degradation or loss of nucleic acids in collected samples leads to inaccurate diagnostic results.

However, the chemical preservation of a wide variety of specimen collections has resulted in a wide variety of different types of transport media, based upon the contents of the specimen collected. For example, urine, stool, swabs from sexually transmitted infections (STIs), and respiratory collections all use different types of transport media.

In addition, very few types of transport media are specially designed for nucleic acid amplification applications, with currently available examples of including Copan eNat (Copan Diagnostics Inc., Carlsbad, CA) and PrimeStore® MTM (Longhorn Vaccines and Diagnostics LLC, Bethesda, MD). However, most transport media designed for nucleic acid amplification applications (NAA-focused transport media) are guanidinium based.

Therefore, there is a need in the art for new and improved types of transport media that are capable of use with a wide variety of specimen/sample collections; capable of preserving the DNA/RNA released from lysis at room temperature during transportation; and are designed for specific NAA applications in Core-Lab facilities. It is to such transport media and methods of using same that the present disclosure is directed.

DETAILED DESCRIPTION

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive.

Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the medical procedures and techniques of, surgery, anesthesia, wound healing, and infectious control described herein are those well-known and commonly used in the art. Standard techniques are used for infection diagnostic and therapeutic applications.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions, kits, and/or methods disclosed herein can be made and executed without undue experimentation in light of the present disclosure. While the compositions, kits, and/or methods have been described in terms of particular embodiments, it will be apparent to those of skill in the art that variations may be applied to the compositions, kits, and/or methods and in the steps or in the sequence of steps of the methods described herein without departing from the concept, spirit, and scope of the present disclosure. All such similar substitutions and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

The use of ordinal number terminology (i.e., "first," "second," "third," "fourth," etc.) is solely for the purpose of differentiating between two or more items and, unless explicitly stated otherwise, is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps. For example, a process, method, article, or apparatus that comprises a list of elements is not necessarily limited to only those elements but may include other elements not expressly listed or inherently present therein.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "sample" as used herein will be understood to include any type of biological sample that may be utilized in accordance with the present disclosure. In certain embodiments, the sample may be any fluidic sample and/or sample capable of being fluidic (e.g., a biological sample mixed with a fluidic substrate). Examples of biological samples that may be utilized include, but are not limited to, whole blood or any portion thereof (i.e., plasma or serum), saliva, sputum, cerebrospinal fluid (CSF), surgical drain fluid, skin, intestinal fluid, intraperitoneal fluid, cystic fluid, sweat, interstitial fluid, extracellular fluid, tears, mucus, bladder wash, urine, swabs, semen, fecal, pleural fluid, nasopharyngeal fluid, combinations thereof, and the like. In particular (but non-limiting) examples, the biological sample may be urine, stool, sexually transmitted infection (STI) swabs, respiratory collections, and the like.

Turning now to the inventive concepts, transport media for sample collection and molecular diagnostic applications are disclosed, as well as kits containing same and methods of production and use thereof. The single reagent design of the transport media allows for the deactivation of pathogens and lysis of organisms present in the collected specimens disposed therein, release of nucleic acids from the specimens, and preservation of DNA/RNA targets at room temperature (or even higher temperatures) for weeks. In addition, the single reagent design of the transport media allows for a larger variety of sample to be collected in collection devices and shipped to core/clinical facilities from remote locations without the need for temperature controls over long periods of time. This is critical for Point-of-Care (POC) business applications and for promoting early and lower diagnostic costs in rural and developing areas, ultimately enhancing the quality of life for patients.

Certain non-limiting embodiments of the present disclosure are directed to a transport medium for sample collection and molecular diagnostic applications. The transport medium A transport medium for sample collection and molecular diagnostic applications, the transport medium comprises one or more of the following ingredients: a chaotropic salt; a buffer; a polysorbate; a zwitterionic surfactant; a PEG (polyethylene glycol); EDTA (ethylenediaminetetraacetic acid); an alcohol; at least one reducing agent; an anti-foaming agent; and SDS (sodium dodecyl sulfate). In certain particular (but non-limiting) embodiments, the transport medium includes two, three, four, five, six, seven, eight, or all nine of the above ingredients.

Each component may be present in the formulation of the transport medium at any concentration that allows the transport medium to function as described herein. For example (but not by way of limitation), each component may be present at a concentration of about 0.001%, about 0.05%, about 0.1%, about 0.5%, about 1.0%, about 1.5%, about 2.0%, about 2.5%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, or higher; in addition, each component may be present at a concentration that falls within a range of two of the above values (i.e., a range from about 0.5% to about 20%, a range of from about 1% to about 10%, etc.).

In other non-limiting examples, each component may be present at a concentration of about 0.01 mM, about 0.05 mM, about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 125 mM, about 150 mM, about 175 mM, about 200 mM, about 225 mM, about 250 mM, about 275 mM, about 300 mM, about 325 mM, about 350 mM, about 375 mM, about 400 mM, about 425 mM, about 450 mM, about 475 mM, about 500 mM, about 525 mM, about 550 mM, about 575 mM, about 600 mM, about 625 mM, about 650 mM, about 657 mM, about 700 mM, about 725 mM, about 750 mM, about 775 mM, about 800 mM, about 825 mM, about 850 mM, about 875 mM, about 900 mM, about 925 mM, about 950 mM, about 975 mM, about 1 M, about 1.5 M, about 2 M, about 2.5 M, about 3 M, about 3.5 M, about 4 M, about 4.5 M, about 5 M, and higher. In addition, each component may be present at a concentration that falls within a range of two of the above values (i.e., a range from about 0.1 mM to about 25 mM, a range of from about 1 mM to about 100 mM, etc.).

Any chaotropic agents known in the art or otherwise contemplated herein may be utilized in accordance with the present disclosure, as long as the transport medium formed therefrom is capable of fully functioning as described herein.

In particular (but non-limiting) embodiments, guanidine thiocyanate is utilized as the chaotropic agent. Guanidine thiocyanate may be present at any concentration that allows the transport medium to function as described herein. Certain non-limiting examples of guanidine thiocyanate concentrations that may be utilized in accordance with the present disclosure include 0.1 M, about 0.2 M, about 0.3 M, about 0.4 M, about 0.5 M, about 0.6 M, about 0.7 M, about 0.8 M, about 0.9 M, about 1 M, about 2 M, about 3 M, about 4 M, about 5 M, about 6 M, about 7 M, about 8 M, about 9 M, about 10 M, and the like, as well as any range formed from two of the above values or from two values that each fall between two of the above values (i.e., a range of from about 1 M to about 10 M, a range of from about 3 M to about 5 M, a range of from about 2.3 M to about 7.7 M, etc.). In a particular (but non-limiting) embodiment, guanidine thiocyanate is present at a concentration of about 3.3 M.

Any buffers known in the art or otherwise contemplated herein may be utilized in accordance with the present disclosure, as long as the transport medium formed therefrom is capable of fully functioning as described herein. Non-limiting buffers that may be utilized in accordance with the present disclosure are sodium acetate (NaOAc) and Tris.

The buffer may be present at any concentration and at any pH that allows the transport medium to function as described herein. Certain non-limiting examples of buffer concentrations that may be utilized in accordance with the present disclosure include about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 125 mM, about 150 mM, about 175 mM, about 200 mM, about 225 mM, about 250 mM, about 275 mM, about 300 mM, about 325 mM, about 350 mM, about 375 mM, about 400 mM, about 425 mM, about 450 mM, about 475 mM, about 500 mM, and the like, as well as any range formed from two of the above values or from two values that each fall between two of the above values (i.e., a range of from about 1 mM to about 500 mM, a range of from about 50 mM to about 200 mM, etc.). Certain non-limiting examples of pH values that may be utilized in accordance with the present disclosure include about 1, about 2, about 3, about 4, about 5, about 6, about 7, about 8, about 9, about 10, about 11, about 12, and the like, as well as any range formed from two of the above values or from two values that each fall between two of the above values (i.e., a pH in a range of from about 4 to about 9, a pH in a range of from about 4 to about 7, etc.).

In a particular (but non-limiting) embodiment, the buffer is sodium acetate or Tris and is present at a concentration of about 100 mM and a pH in a range of from about 5 to about 8.

Any polysorbates known in the art or otherwise contemplated herein may be utilized in accordance with the present disclosure. In particular (but non-limiting) embodiments, the polysorbate is Polysorbate-20.

The polysorbate may be present at any concentration that allows the transport medium to function as described herein. Certain non-limiting examples of polysorbate concentrations that may be utilized in accordance with the present disclosure include about 0.1%, about 0.5%, about 1.0%, about 1.5%, about 2.0%, about 2.5%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, and the like, as well as any range formed from two of the above values or from two values that each fall between two of the above values (i.e., a range of from about 0.1% to about 20%, a range of from about 5% to about 15%, etc.). In a particular (but non-limiting) embodiment, the polysorbate is present at a concentration in a range of from about 8% to about 10%.

Any zwitterionic surfactants known in the art or otherwise contemplated herein may be utilized in accordance with the present disclosure. In particular (but non-limiting) embodiments, the zwitterionic surfactant is CHAPS (3-((3-cholamidopropyl) dimethylammonio)-1-propanesulfonate).

The zwitterionic surfactant may be present at any concentration that allows the transport medium to function as described herein. Certain non-limiting examples of zwitterionic surfactant concentrations that may be utilized in accordance with the present disclosure include about 0%, about 0.1%, about 0.5%, about 1.0%, about 1.5%, about 2.0%, about 2.5%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, and the like, as well as any range formed from two of the above values or from two values that each fall between two of the above values (i.e., a range of from about 0.1% to about 10%, a range of from about 0.1% to about 5%, etc.).

Any polyethylene glycols (PEGs) known in the art or otherwise contemplated herein may be utilized in accordance with the present disclosure. In particular (but non-limiting) embodiments, the PEG is PEG8000.

The PEG may be present at any concentration that allows the transport medium to function as described herein. Certain non-limiting examples of PEG concentrations that may be utilized in accordance with the present disclosure include about 0%, about 0.1%, about 0.5%, about 1.0%, about 1.5%, about 2.0%, about 2.5%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, and the like, as well as any range formed from two of the above values or from two values that each fall between two of the above values (i.e., a range of from about 1% to about 5%, etc.).

EDTA may be present at any concentration that allows the transport medium to function as described herein. Certain non-limiting examples of EDTA concentrations that may be utilized in accordance with the present disclosure include about 0.01 mM, about 0.05 mM, about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 2 mM, about 3 mM, about 4 mM, about 5 mM, about 6 mM, about 7 mM, about 8 mM, about 9 mM, about 10 mM, and the like, as well as any range formed from two of the above values or from two values that each fall between two of the above values (i.e., a range of from about 0.01 mM to about 1 mM, etc.).

Any alcohols known in the art or otherwise contemplated herein may be utilized in accordance with the present disclosure. In particular (but non-limiting) embodiments, the alcohol is ethanol.

The alcohol may be present at any concentration that allows the transport medium to function as described herein. Certain non-limiting examples of alcohol concentrations that may be utilized in accordance with the present disclosure include about 1.0%, about 1.5%, about 2.0%, about 2.5%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, and the like, as well as any range formed from two of the above values or from two values that each fall between two of the above values (i.e., a range of from about 1% to about 40%, a range of from about 10% to about 30%, etc.).

In a particular (but non-limiting) embodiment, the alcohol is ethanol, and the ethanol is present in the transport media at a concentration of about 20%.

Any reducing agents known in the art or otherwise contemplated herein may be utilized in accordance with the present disclosure, so long as the transport medium containing same can function as described herein. In particular (but non-limiting) embodiments, the reducing agent is TCEP (Tris(2-carboxyethyl) phosphine)) and/or DTT (dithiothreitol).

The reducing agent may be present at any concentration that allows the transport medium to function as described herein. Certain non-limiting examples of reducing agent concentrations that may be utilized in accordance with the present disclosure include about 0.01 mM, about 0.05 mM, about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 2 mM, about 3 mM, about 4 mM, about 5 mM, about 6 mM, about 7 mM, about 8 mM, about 9 mM, about 10 mM, about 15 mM, about 20 mM, and the like, as well as any range formed from two of the above values or from two values that each fall between two of the above values (i.e., a range of from about 0.1 mM to about 20 mM, a range of from about 1 mM to about 10 mM, etc.).

Any anti-foaming agents known in the art or otherwise contemplated herein may be utilized in accordance with the present disclosure. In particular (but non-limiting) embodiments, the anti-foaming agent is Antifoam-A (Sigma-Aldrich, St. Louis, MO), Antifoam 204, or another silicone-based product.

The anti-foaming agent may be present at any concentration that allows the transport medium to function as described herein. Certain non-limiting examples of anti-foaming agent concentrations that may be utilized in accordance with the present disclosure include about 0.001%, about 0.00125%, about 0.002%, about 0.0025%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 4%, about 5%, about 6%, about 7%, about 8%, about 9%, about 10%, and the like, as well as any range formed from two of the above values or from two values that each fall between two of the above values (i.e., a range of from about 0.001% to about 0.1%, a range of from about 0.01% to about 0.8%, etc.).

In certain particular (but non-limiting) embodiments, the transport medium is capable of use with at least two different types of biological samples.

In certain particular (but non-limiting) embodiments, the transport medium substantially deactivates at least one infectious pathogen present in a biological sample and substantially releases or lyses at least one bacteria and virus present in a biological sample.

In certain particular (but non-limiting) embodiments, the transport medium substantially preserves DNA and/or RNA for a period of at least about 15 days at room temperature.

Certain non-limiting embodiments of the present disclosure are directed to a transport medium for sample collection and molecular diagnostic applications, wherein the transport medium comprises one or more of the following ingredients: guanidine thiocyanate in a sodium acetate buffer; Polysorbate-20; CHAPS; EDTA (ethylenediaminetetraacetic acid); alcohol; a reducing agent; PEG8000; and an anti-foaming reagent. In certain particular (but non-limiting) embodiments, the transport medium includes two, three, four, five, six, seven, or all eight of the above ingredients.

In addition, the kit may further contain one or more other element(s) or reagent(s) for performing biological sample collection(s) and/or molecular diagnostic application(s) in accordance with the present disclosure. For example (but not by way of limitation), the kit may further contain at least one sample collection device, such as (but not limited to), a single format, multi-collection device.

The nature of these additional reagent(s) will depend upon various factors such as (but not limited to) the type of biological sample and the molecular diagnostic assay format, and identification thereof is well within the skill of one of ordinary skill in the art; therefore, no further description thereof is deemed necessary. Also, the various components/reagents present in the kit may each be in separate containers/compartments, or various components/reagents can be combined in one or more containers/compartments, depending on the cross-reactivity and stability of the components/reagents. In addition, the kit may include a set of written instructions explaining how to use the kit. A kit of this nature can be used in any of the methods described or otherwise contemplated herein.

Certain non-limiting embodiments of the present disclosure are directed to a mixture containing a biological sample disposed within any of the transport media disclosed or otherwise contemplated herein.

By disposing the biological sample in the transport media, nucleic acid present in the sample is stable for an extended period of time at room temperature, and one or more nucleic acid assay targets present in the biological sample is not substantially degraded during that period. For example (but not by way of limitation), nucleic acid present in the sample may be stable for a period of at least about 15 days at room temperature, and the at least one nucleic acid assay target present in the biological sample is not substantially degraded during that period. Also, the nucleic acid present in the biological sample may be stable within the mixture for a period of at least about 25 days at room temperature, and the at least one nucleic acid assay target present in the biological sample is not substantially degraded during that period.

The biological sample may be any biological sample disclosed or otherwise contemplated herein that contains one or more DNA/RNA targets that need to be preserved for subsequent detection via nucleic acid amplification (NAA). For example (but not by way of limitation), the biological sample may be selected from the group consisting of urine, stool, sexually transmitted infection (STI) swabs, respiratory collections, blood or any portion thereof, saliva, sputum, cerebrospinal fluid (CSF), surgical drain fluid, intestinal fluid, intraperitoneal fluid, cystic fluid, sweat, interstitial fluid, extracellular fluid, tears, mucus, bladder wash, urine, swabs, semen, pleural fluid, nasopharyngeal fluid, and combinations thereof.

Certain non-limiting embodiments of the present disclosure are directed to a method of producing any of the transport media disclosed or otherwise contemplated herein. In the method, the individual ingredients of the transport medium are combined to form the transport medium.

Certain non-limiting embodiments of the present disclosure are directed to a method of using any of the transport media disclosed or otherwise contemplated herein. For example (but not by way of limitation), the method includes the step of disposing a biological sample in any of the transport medium disclosed or otherwise contemplated herein to form a mixture.

In certain particular (but non-limiting) embodiments, the method includes one or more additional steps selected from: shipping the mixture to a clinical facility; storing the mixture for at least one week; and/or performing at least one molecular diagnostic assay (such as, but not limited to, at least one nucleic acid amplification step) on the mixture.

Certain non-limiting embodiments of the present disclosure are directed to a kit containing any of the transport media disclosed or otherwise contemplated herein.

EXAMPLES

Examples are provided hereinbelow. However, the present disclosure is to be understood to not be limited in its application to the specific experimentation, results, and laboratory procedures disclosed herein after. Rather, the Examples are simply provided as one of various embodiments and are meant to be exemplary, not exhaustive.

The transport media of the present disclosure allows for the deactivation of pathogens and lysis of organisms (i.e., bacteria and viruses) present in the collected specimens disposed therein, release of nucleic acids from the specimens, and preservation of DNA/RNA targets at room temperature (or even higher temperatures) for weeks.

The transport media of the present disclosure were tested with a wide variety of sample matrices (including, but not limited to, stool, urine, simulated nasal fluid, and simulated STI matrix) and demonstrated to have room temperature stability for 25-30 days in an accelerated stability test format. Also, the extreme conditions of −20° C. freeze thaw 3 times, and 45° C. for 2 hours storage were also tested in order to demonstrate the robustness of the transport media of the present disclosure in transport conditions lacking environmental control measures.

Multiple purposes and tasks can be performed in the one liquid of the transport media produced in accordance with the present disclosure. Guanidine thiocyanate and alcohol can deactivate a wide range of pathogens during transportation, thereby reducing risk of infection and increasing safety handling. Components like guanidine thiocyanate, Polysorbate-20, CHAPS, and/or PEG8000 have been used in part because of their lysis function, which lyses pathogens and releases nucleic acids therefrom. Multiple components of the transport media are able to enhance the stability of and preserve target RNA/DNA by deactivating the enzymes which could potentially denature nucleic acids. In addition, the optional antifoaming agent makes transportation and liquid handling much easier and reduces the amount of foaming, as well as reduces error from automated liquid handling.

Loading of this transport media on a Multi-Collection Device (MCD) allows for collection of a wide variety of specimens specially designed for a particular NAA system. The transport media is able to deactivate infectious pathogens and release or lyse the bacteria and viruses, then preserve the DNA/RNA released from lysis at room temperature during transportation. Once the samples arrive at the core facility, the sample/transport media mixture is immediately available for nucleic acid concentration and extraction. The transport media itself serves multiple roles to streamline the workflow, including collection, processing, storage, and preservation, and also protects personnel from viable pathogenic exposure. In addition, once the samples present in the transport media arrive at the core facility, they will be available straightaway for nucleic acids concentration and extraction. These features of the transport media of the present disclosure greatly increase the workflow and efficiencies of the steps of specimen collection, transportation, screening, and diagnostics.

Various Transport Media produced in accordance with the present disclosure are shown in Table 1 and labeled as ATM1-ATM14. Other ATMs may be labeled as "+AFA," which refers to the addition of 0.05% of an anti-foaming agent to the ATM listed in Table 1.

These various transport media were tested with a wide variety of sample types and demonstrated to possess room temperature stability for 25-30 days in an accelerated stability test format. Some of the various viruses/bacteria/pathogens, sample matrices, and storage conditions tested are shown in Table 2. The transport media/microorganisms/storage conditions were tested against various commercially available reagents, including commercial BD universal transport media; OTS media such as (but not limited to) Mawi, Puritan PurSafe, and Copan's Eswab and Mswab; OTS-Longhorn; Remel M6; eNat; and Spectrum.

The sample types tested included herpes simplex virus (HSV), human immunodeficiency virus (HIV), and chlamydia/gonorrhea (CT/GC) in an STI panel; both DNA and RNA pathogens in a respiratory panel; viral, bacterial, and parasitic pathogens in a gastrointestinal panel; and BK virus (BKV) in a transplant panel. The transport media of the present disclosure were also tested with a wide variety of sample matrices (including, but not limited to, stool, urine, plasma, simulated nasal fluid, simulated STI matrix) and demonstrated to possess room temperature stability for 25-30 days in an accelerated stability test format. Also, the extreme conditions of –20° C. freeze thaw 3 times, and 45° ods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

| Component | Function | Transport Media 1 (ATM1) | Transport Media 2 (ATM2) | Transport Media 3 (ATM3) | Transport Media 4 (ATM4) | Transport Media 5 (ATM5) | Transport Media 6 (ATM6) | Transport Media 7 (ATM7) |
|---|---|---|---|---|---|---|---|---|
| Guanidine Thiocyanate | Chaotropic salt | 3.3M | 3.3M | 3.3M | 3.3M | 3.3M | 3.3M | 3.3M |
| Sodium Acetate/Tris | Buffer | 100 mM pH 6 (NaOAc) | 100 mM pH 8 (Tris) | 100 mM pH 6 (NaOAc) | 100 mM pH 6 (NaOAc) | 100 mM pH 6 (NaOAc) | 100 mM pH 5 (NaOAc) | 100 mM pH 6 (NaOAc) |
| Tween 20 (Polysorbate 20) | Nonionic surfactant | 10% | 10% | 8% | 8% | 10% | 8% | 8% |
| PEG8000 | Nonionic surfactant | 0% | 0% | 0% | 0% | 1.5% | 0% | 0% |
| SDS | Anionic surfactant | 0.20% | 0.20% | 0% | 0% | 0% | 0% | 0% |
| CHAPS | Zwitterionic surfactant | 0% | 0% | 2% | 2% | 0% | 2% | 1% |
| EDTA | Metal Chelator | 0.1 mM | 0.1 mM | 0.1 mM | 0.1 mM | 0.1 mM | 0.1 mM | 0.1 mM |
| Ethanol | Co-solvent | 20% | 20% | 20% | 20% | 20% | 20% | 20% |
| DTT/TCEP | Reducing Agent | 2 mM (TCEP) | 2 mM (TCEP) | 1 mM (DTT) | 1 mM (TCEP) | 1 mM (TCEP) | 1 mM (DTT) | 1 mM (DTT) |

| Component | Function | Transport Media 7A (ATM7A) | Tranport Media 8 (ATM8) | Transport Media 9 (ATM9) | Transport Media 10 (ATM10) | Transport Media 11 (ATM11) | Transport Media 12 (ATM12) | Transport Media 13 (ATM13) | Transport Media 14 (ATM14) |
|---|---|---|---|---|---|---|---|---|---|
| Guanidine Thiocyanate | Chaotropic salt | 3.3M | 3.3M | 3.3M | 3.3M | 3.3M | 3.3M | 3.3M | 3.3M |
| Sodium Acetate/Tris | Buffer | 100 mM pH 6 (NaOAc) | 100 mM pH 6 (NaOAc) | 100 mM pH 6 (NaOAc) | 100 mM pH 6 (NaOAc) | 100 mM pH 6 (NaOAc) | 100 mM pH 6 (NaOAc) | 100 mM pH 6 (NaOAc) | 100 mM pH 6 (NaOAc) |
| Tween 20 (Polysorbate 20) | Nonionic surfactant | 8% | 5% | 3% | 1% | 8% | 8% | 8% | 8% |
| PEG8000 | Nonionic surfactant | 0% | 0% | 0% | 0% | 0% | 0% | 0% | 0% |
| SDS | Anionic surfactant | 0% | 0% | 0% | 0% | 0% | 0% | 0% | 0% |
| CHAPS | Zwitterionic surfactant | 1% | 1% | 1% | 1% | 1% | 1% | 1% | 1% |
| EDTA | Metal Chelator | 0.1 mM | 0.1 mM | 0.1 mM | 0.1 mM | 0.1 mM | 0.1 mM | 0.1 mM | 0.1 mM |
| Ethanol | Co-solvent | 20% | 20% | 20% | 20% | 20% | 20% | 20% | 20% |
| DTT/TCEP | Reducing Agent | 1 mM (TCEP) | 1 mM (TCEP) | 1 mM (TCEP) | 1 mM (TCEP) | 1 mM (TCEP) | 3 mM (TCEP) | 5 mM (TCEP) | 20 mM (TCEP) |

C. for 2 hours storage were tested in order to demonstrate the robustness of these transport media in transport conditions which could lack of environmental control measures.

Table 3 lists a summary of relative Ct values obtained for various pathogens after 24/28 days when stored in the transport media of the present disclosure or a commercially available lysis buffer. In the experiments outlined in Table 3, eleven (11) microorganisms were tested, and the samples processed in the transport media of the present disclosure resulted in the same or lower Ct values than samples processed in lysis buffer. These results demonstrate that the transport media of the present disclosure outperformed the commercially available media.

Thus, in accordance with the present disclosure, there have been provided compositions and kits, as well as meth-

TABLE 2

Various Microorganisms, Sample Matrices, and Storage Conditions Tested with the Transport Media of the Present Disclosure

| Micro-organism | Sample Matrix | Transport Media | Storage Conditions |
|---|---|---|---|
| EBV | None | ATM1, ATM2, ATM3 | RT and 4° C. for 14 days |
| HIV | None | ATM1, ATM2, ATM3 | RT and 4° C. for 25 days |
| EBV | Plasma as simulated matrix | ATM3, ATM4, ATM5 | RT and 4° C. for 25 days |

TABLE 2-continued

Various Microorganisms, Sample Matrices, and Storage
Conditions Tested with the Transport Media of the Present Disclosure

| Microorganism | Sample Matrix | Transport Media | Storage Conditions |
|---|---|---|---|
| HIV | None or Plasma as simulated matrix | ATM3, ATM4, ATM5, with and without 2% plasma | RT for 2 days |
| HIV and/or HSV | Stool | ATM3 | RT for 14 days |
| E. coli | Stool | ATM3, ATM6, ATM7 | RT for 26 days |
| HSV-1 | Stool | ATM3, ATM6, ATM7 | RT for 26 days |
| HSV-2 | Stool | ATM3, ATM6, ATM7 | RT for 26 days |
| HSV-1 | None | ATM3, ATM6, ATM7 | RT for 23 days |
| HSV-1, HSV-2 | | ATM3, ATM7 | Freeze-thaw 3 cycles at −20° C. |
| HSV-1, HSV-2 | | ATM3, ATM7 | 45° C. for >3 hours |
| HSV-1, HSV-2 | Clinical Swab pooled media | ATM3, ATM7 | RT for 30 days |
| HSV-1, HSV-2 | Stool | ATM3, ATM7 | RT for 26 days |
| HSV-1, HSV-2 | Clinical Swab pooled media | ATM3, ATM7 | RT for 30 days |
| HSV-1, HSV-2 | Stool Challenging Medium | ATM3, ATM7 | RT at 30 days |
| HSV-1, HSV-2 | Clinical Aptima Swab Medium | ATM3, ATM7 | RT at 30 days |
| CT/GC | Urine | ATM3, ATM5, ATM6, ATM7, ATM7A, ATM7A + AFA, ATM8, ATM9, ATM10 | RT at 30 days |
| CT/GC | Urine | ATM3, ATM7 | Freeze-thaw 3 cycles at −20° C. |
| CT/GC | Urine | ATM3, ATM7 | 45° C. for >3 hours |
| BKV | Urine | ATM3, ATM5, ATM6, ATM7 | RT for 26 days |
| BKV | Urine | ATM3, ATM7 | Freeze-thaw 3 cycles at −20° C. |
| BKV | Urine | ATM3, ATM7 | 45° C. for >3 hours |
| C. difficile | Stool | ATM3, ATM5, ATM6, ATM7 | RT for 24 days |
| C. difficile | Stool | ATM3, ATM7 | Freeze-thaw 3 cycles at −20° C. |
| C. difficile | Stool | ATM3, ATM7 | 45° C. for >3 hours |
| E. coli (933 ETEC) | Stool | ATM3, ATM5, ATM6, ATM7A + AFA | RT for 24 days |
| Human Adenovirus 40 | Stool | ATM3, ATM5, ATM6, ATM7A + AFA | RT for 28 days |
| Norovirus Gpll | Stool | ATM3, ATM5, ATM6, ATM7A + AFA | RT for 28 days |
| E. histolytica | Stool | ATM3, ATM5, ATM6, ATM7A + AFA | RT for 28 days |
| E. coli (933 ETEC) | | ATM3, ATM7A + AFA | Freeze-thaw 3 cycles at −20° C. |
| E. coli (933 ETEC) | | ATM3, ATM7A + AFA | 45° C. for >3 hours |
| Adenovirus 40 | | ATM3, ATM7A + AFA | Freeze-thaw 3 cycles at −20° C. |
| Adenovirus 40 | | ATM3, ATM7A + AFA | 45° C. for >3 hours |
| Norovirus Gpll | | ATM3, ATM7A + AFA | Freeze-thaw 3 cycles at −20° C. |

TABLE 2-continued

Various Microorganisms, Sample Matrices, and Storage
Conditions Tested with the Transport Media of the Present Disclosure

| Microorganism | Sample Matrix | Transport Media | Storage Conditions |
|---|---|---|---|
| Norovirus Gpll | | ATM3, ATM7A + AFA | 45° C. for >3 hours |
| E. histolytica | | ATM3, ATM7A + AFA | Freeze-thaw 3 cycles at −20° C. |
| E. histolytica | | ATM3, ATM7A + AFA | 45° C. for >3 hours |
| C. difficile | Urine | ATM3, ATM7 | RT for 28 days |
| HSV-1 | Urine | ATM3, ATM7 | RT for 28 days |
| HSV-2 | Urine | ATM3, ATM7 | RT for 28 days |
| Rhinovirus 1A | | ATM3, ATM4, ATM5, ATM6, ATM7, ATM7A, ATM7A + AFA, ATM8, ATM9, ATM10, ATM11 + AFA | RT for 24-35 days |
| RSV Type A | | ATM3, ATM4, ATM5, ATM6, ATM7, ATM7A, ATM7A + AFA, ATM8, ATM9, ATM10, ATM11 + AFA | RT for 24-35 days |
| Coronavirus 229E | | ATM3, ATM4, ATM5, ATM6, ATM7, ATM7A, ATM7A + AFA, ATM8, ATM9, ATM10, ATM11 + AFA | RT for 24-35 days |
| Human Parainfluenza Type 1 | | ATM3, ATM4, ATM5, ATM6, ATM7, ATM7A ATM7A + AFA, ATM8, ATM9, ATM10, ATM11 + AFA | RT for 24-35 days |
| Influenza B (Florida/02/06) | | ATM3, ATM4, ATM5, ATM6, ATM7, ATM7A, ATM7A + AFA, ATM8, ATM9, ATM10, ATM11 + AFA | RT for 24-35 days |
| RSV Type B | | ATM3, ATM4, ATM5, ATM6, ATM7, ATM7A, ATM7A + AFA, ATM8, ATM9, ATM10 | RT for 24-35 days |
| Influenza A (H1N1) | | ATM3, ATM4, ATM5, ATM6, ATM7, ATM7A, ATM7A + AFA, ATM8, ATM9, ATM10, ATM11 + AFA | RT for 24-35 days |
| M. pneumoniae | | ATM3, ATM4, ATM5, ATM6, ATM7, ATM7A, ATM7A + AFA, ATM8, ATM9, ATM10, ATM11 + AFA | RT for 24-35 days |
| M. smegmatis | Sputum | ATM7A, ATM7A + AFA, ATM12, ATM13, ATM14 | |
| | Artificial sputum 15% mucin | ATM7A, ATM7A + AFA, ATM12, ATM13, ATM14 | |

*Raw data can be found priority application U.S. Ser. No. 63/013,257 (the entire contents of which are expressly incorporated herein by reference)

TABLE 3

| Time Points | Relative Ct Value | | | |
| --- | --- | --- | --- | --- |
| | Day 0 | | Day 24/28 | |
| Pathogens | Lysis Buffer | ATMs | Lysis Buffer | ATMs |
| *C. difficile* | Same | Same | Higher | Lower |
| HSV-1 | Lower | Higher | Same | Same |
| HSV-2 | Lower | Higher | Same | Same |
| *M. pneumoniae* | Same | Same | Same | Same |
| Rhinovirus | Same | Same | Same | Same |
| Flu A | Same | Same | Higher | Lower |
| Flu B | Higher | Lower | Higher | Lower |
| RSV A | Same | Same | Higher | Lower |
| RSV B | Higher | Lower | Higher | Lower |
| Parainfluenza | Lower | Higher | Higher | Lower |
| Coronavirus | Same | Same | Same | Same |

What is claimed is:

1. A transport medium for sample collection and molecular diagnostic applications, the transport medium comprising:

guanidine thiocyanate in a sodium acetate buffer, wherein the guanidine thiocyanate is present at a concentration in a range of from about 3M to about 4M;

a polysorbate, wherein the polysorbate is present at a concentration in the range of from about 0.1% to about 20%;

CHAPS (3-((3-cholamidopropyl)dimethylammonio)-1-propanesulfonate), wherein CHAPS is present at a concentration in a range of from about 0.1% to about 5%;

EDTA (ethylenediaminetetraacetic acid);

an alcohol, wherein the alcohol is present at a concentration in a range of from about 1% to about 40%; and at least one reducing agent selected from the group consisting of TCEP (Tris(2-carboxyethyl) phosphine)), DTT (dithiothreitol), and a combination thereof, wherein the transport medium substantially preserves DNA and/or RNA from the biological sample for a period of at least about 15 days to 30 days at room temperature.

2. The transport medium of claim 1, wherein the guanidine thiocyanate is present at a concentration in a range of from about 3M to about 4 M.

3. The transport medium of claim 1, wherein the sodium acetate buffer is present at a concentration in a range of from about 50 mM to about 200 mM and at a pH in a range of from about 4 to about 7.

4. The transport medium of claim 1, wherein the polysorbate is Polysorbate-20.

5. The transport medium of claim 1, wherein the alcohol is ethanol.

6. The transport medium of claim 1, further comprising at least one additional ingredient selected from the group consisting of SOS (sodium dodecyl sulfate), polyethylene glycol (PEG), an anti-foaming agent, and combinations thereof.

7. A kit, comprising:

the transport medium of claim 1.

8. The kit of claim 7, further comprising at least one sample collection device.

9. The kit of claim 8, wherein the sample collection device is a single format, multi-collection device.

10. A mixture, comprising:

a biological sample; and the transport medium of claim 1, wherein the biological sample is disposed within the transport medium.

11. The mixture of claim 10, wherein the biological sample is selected from the group consisting of urine, stool, sexually transmitted infection (STI) swabs, respiratory collections, blood or any portion thereof, saliva, sputum, cerebrospinal fluid (CSF), surgical drain fluid, intestinal fluid, intraperitoneal fluid, cystic fluid, sweat, interstitial fluid, extracellular fluid, tears, mucus, bladder wash, urine, swabs, semen, pleural fluid, nasopharyngeal fluid, and combinations thereof.

12. A method, comprising the steps of:

disposing a biological sample in the transport medium of claim 1 to form a mixture.

13. The method of claim 12, further comprising at least one step selected from the group consisting of:

shipping the mixture to a clinical facility;

storing the mixture for at least one week; and performing at least one nucleic acid amplification step on the mixture.

\* \* \* \* \*